United States Patent [19]

Lee

[11] Patent Number: 4,749,696

[45] Date of Patent: Jun. 7, 1988

[54] HYDROXY-[1-SUBSTITUTED CARBONYL-2-(OR 3-) PIPERIDINYL METHOXY]PHOSPHINYLOXY]-N,N,N-TRIALKYLALKANEAMINIUM HYDROXIDE INNER SALT OXIDES HAVING ANTITUMOR ACTIVITY

[75] Inventor: Mark L. Lee, Lake Hopatcong, N.J.

[73] Assignee: Sandoz Pharm. Corp., E. Hanover, N.J.

[21] Appl. No.: 902,279

[22] Filed: Aug. 29, 1986

Related U.S. Application Data

[63] Continuation-in-part of Ser. No. 771,288, Aug. 30, 1985, abandoned.

[51] Int. Cl.$^4$ .................. C07F 9/65; A01N 31/675
[52] U.S. Cl. ........................................ 514/89; 546/22
[58] Field of Search ............................ 546/22; 514/89

[56] References Cited

U.S. PATENT DOCUMENTS 4,567,167  1/1986  Karanewsky .................. 514/89
4,650,791  3/1987  Nomura et al. ................ 514/82

*Primary Examiner*—Alan L. Rotman
*Attorney, Agent, or Firm*—Gerald D. Sharkin; Robert S. Honor; Joseph J. Borovian

[57] ABSTRACT

The invention discloses hydroxy-[1-substituted carbonyl-2-(or 3-) piperidinyl methoxy]phosphinyloxy]-N,N,N-trilkylalkaneaminium hydroxide inner salt oxides useful as antitumor agents, pharmaceutical compositions containing said compounds as an active ingredient thereof and a method of using such compositions for treating tumors.

5 Claims, No Drawings

HYDROXY-[1-SUBSTITUTED CARBONYL-2-(OR 3-) PIPERIDINYL METHOXY]PHOSPHINYLOXY]-N,N,N-TRIALKYLALKANEAMINIUM HYDROXIDE INNER SALT OXIDES HAVING ANTITUMOR ACTIVITY

This application is a continuation-in-part of U.S. patent application Ser. No. 771,288, filed Aug. 30, 1985, now abandoned.

The present invention relates to certain hydroxy [1-substituted carbonyl-2-(or 3-) piperidinyl methoxy] phosphinyloxy]-N,N,N-trialkylalkaneaminium hydroxide inner salt oxides and to their use as anti-tumor agents. The invention also relates to pharmaceutical compositions containing the aforementioned compounds as an active ingredient thereof and to the method of using such compositions for treating tumors.

Leukemia, as well as other malignancies of unknown origin including ascitic tumors, has occupied the attention of research organizations for many years and until most recently without appreciable success. Today, many types of tumors can be effectively treated with drugs. In this connection, U.S. Pat. No. 4,119,714 discloses certain etherlysolecithins useful in influencing and controlling the interfacial properties of cell membranes, U.S. Pat. No. 4,393,052 discloses novel anthracycline glycosides useful in treating certain tumors, U.S. Pat. No. 4,393,064 discloses the use of 10-deazaminepterin in treating leukemia and ascitic tumors, U.S. Pat. No. 4,396,553 is directed to tetrahydronaphthalene and indane compounds which are useful as tumor inhibiting agents and U.S. Pat. No. 4,426,525 discloses certain tridecyloxy or tetradecyloxy propane derivatives useful in inhibiting the multiplication of tumor cells. In addition, Belgian Pat. Nos. 854,269 and 854,270 disclose anti-tumor lysolecithin compositions effective against Ehrlich's Ascites methylcholanthrene-induced tumors and myelomas.

The essence of the present invention is the discovery that certain hydroxy-[1-substituted carbonyl-2-(or 3-) piperidinyl methoxy]phosphinyloxy]-N,N,N-trialkylalkaneaminium hydroxide inner salt oxides of formula I,

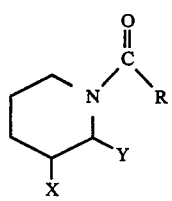

where
R is $C_{12}-C_{24}$ alkyl, alkenyl or alkynyl; or $C_{12}-C_{24}$ alkoxy, alkenoxy or alkynoxy; and
one of X and Y is hydrogen and the other is a group Q

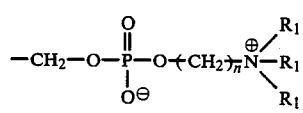

where each $R_1$, independently, is $C_1-C_3$ alkyl and n is an integer 2 to 8; are useful as anti-tumor agents.

Included among the compounds of formula I are the compounds of subclass Ia:

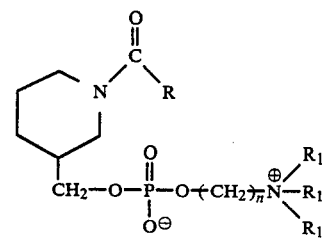

where R, each $R_1$ and n are as defined above.

The preferred compounds of subclass Ia are compounds of formula Ia':

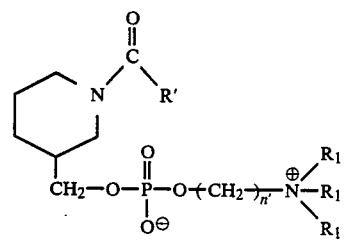

where
R' is $C_{12}-C_{20}$ alkyl, alkenyl or alkynyl; or $C_{12}-C_{20}$ alkoxy, alkenoxy or alkynoxy;
n' is an integer 2 to 6;
and each $R_1$ is as defined above.

The more preferred compounds of subclass Ia are compounds of formula Ia":

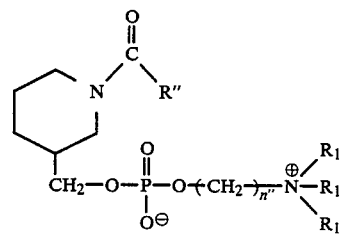

where
R" is $C_{12}-C_{18}$ alkyl, alkenyl or alkynyl; or $C_{12}-C_{18}$-alkoxy, alkenoxy or alkynoxy;
n" is an integer 2 to 4; and each $R_1$ is as defined above.
The even more preferred compounds of subclass Ia are compounds of formula Ia''':

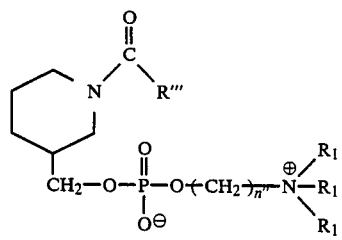

where
R''' is $C_{12}-C_{18}$ alkoxy, alkenoxy or alkynoxy; and n" and each $R_1$ are as defined above.

Also included among the compounds of formula I are the compounds of subclass Ib:

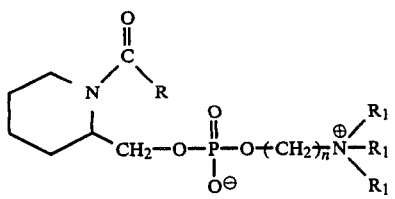

where R, each $R_1$ and n are as defined above.

The preferred compounds of subclass Ib are compounds of formula Ib′:

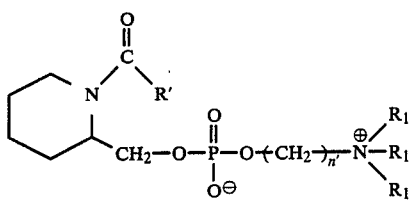

where R′, n′ and each $R_1$ are as defined above.

The more preferred compounds of subclass Ib are compounds of formula Ib″:

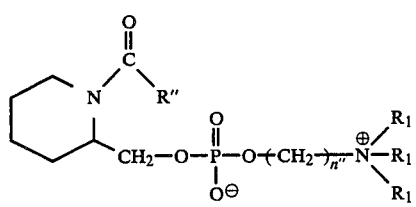

where R″, n″ and each $R_1$ are as defined above.

The even more preferred compounds of subclass Ib are compounds of formula Ib‴:

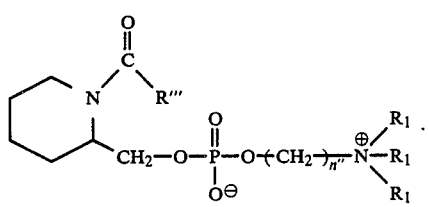

where R‴, n″ and each $R_1$ are as defined above.

In the compounds of formula I and the compounds of subclasses Ia and Ib, including the preferred embodiments of said subclasses (i.e., compounds of the formulae Ia′, Ia″, Ia‴, Ib′, Ib″ and Ib‴), the alkyl, alkenyl, alkynyl, alkoxy, alkenoxy and alkynoxy groups are either straight or branched chain. Moreover, in the alkenyl groups, the double bond is separated from the carbonyl group by at least one carbon atom not participating in the double bond, whereas in the alkenoxy groups, the double bond is separated from the oxygen atom of said groups by at least one carbon atom not participating in the double bond. In the alkynyl groups, the triple bond is separated from the carbonyl group by at least one carbon atom not participating in the triple bond, whereas in the alkynoxy groups, the triple bond is separated from the oxygen atom of said groups by at least one carbon atom not participating in the triple bond.

Especially preferred compounds are those of subclass Ia, including the preferred embodiments of said subclass, i.e., compounds of formulae Ia′, Ia″ and Ia‴. The more especially preferred compounds of subclass Ia are those of formula Ia‴ where R‴ is n-$C_{12}$-$C_{18}$ alkoxy, alkenoxy or alkynoxy, the location of the double and triple bonds, respectively, in the latter two groups is as indicated above. The most especially preferred compounds of subclass Ia are those of formula Ia‴ where R‴ is n-$C_{12}$-$C_{18}$ alkoxy.

The compounds of subclass Ia may be prepared according to the following reaction scheme:

REACTION A

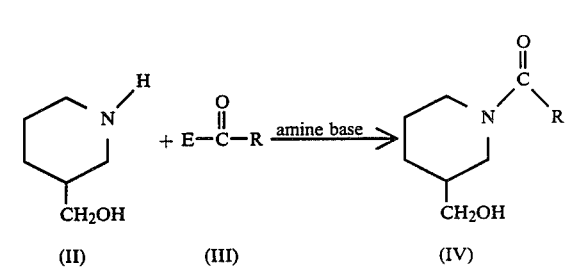

where E is chloride, bromide or iodide and R is as defined above.

REACTION B

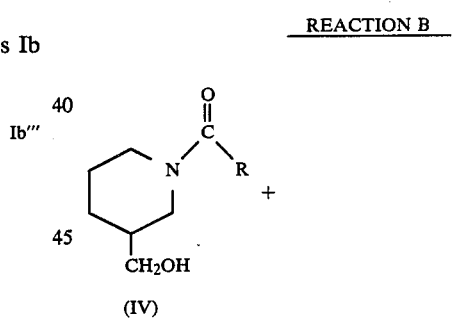

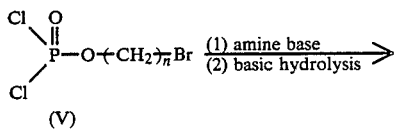

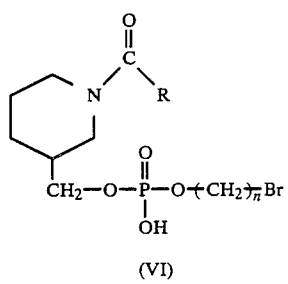

where R and n are as defined above.

REACTION C

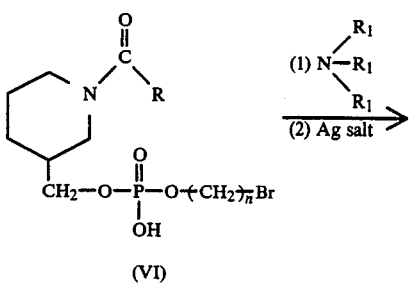

(VI)

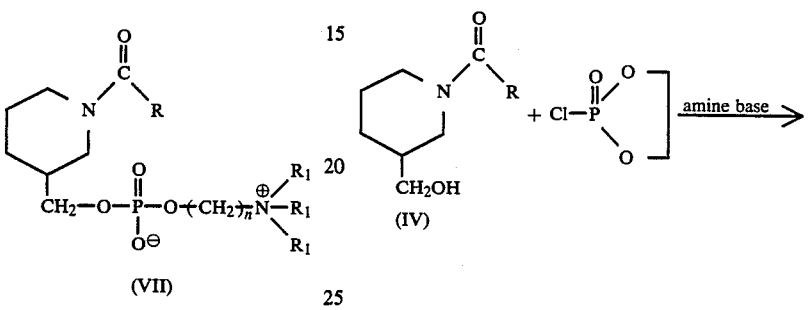

(VII)

where R, each $R_1$ and n are as defined above.

With respect to the individual reactions, Reaction A concerns the reaction of a compound of formula II with a carboxylic acid halide of formula III in the presence of an amine base such as pyridine or a trialkylamine, preferably triethylamine, to yield a compound of formula IV. This reaction is optionally conducted in the presence of an inert, organic solvent, e.g. an aromatic hydrocarbon such as benzene or toluene or an aliphatic halohydrocarbon such as chloroform or dichloromethane at a temperature of from −20° to 30° C. for a period of between 1 and 24 hours.

Reaction B involves the reaction of a compound prepared in Reaction A, i.e., a compound of formula IV, with a compound of formula V, i.e., a bromoalkoxydichlorophosphate compound, e.g., 2-bromoethoxydichlorophosphate, in the presence of an amine base, such as pyridine or triethylamine. The reaction is conveniently carried out in an inert, organic solvent, e.g., an aromatic hydrocarbon such as benzene, toluene or xylene or an aliphatic halohydrocarbon such as chloroform or dichloromethane. As to reaction temperatures and times, they are analogous to those set forth in Reaction A.

The second part of Reaction B involves subjecting the product produced in the first part to basic hydrolysis, e.g., by suspending the product in water. The hydrolysis is conveniently carried out at a temperature of from 20° C. to 100° C. for a period of from 15 minutes to about 3 hours to yield a compound of formula VI.

The last reaction, viz., Reaction C, is concerned with the reaction of a compound prepared in Reaction B, i.e., a compound of formula VI, with trialkylamine in the presence of an inert, organic solvent, e.g., an aromatic hydrocarbon such as benzene or toluene, an aliphatic halohydrocarbon such as chloroform or dichloromethane or a lower alkyl nitrile such as acetonitrile. As to reaction conditions, the reaction is generally carried out a temperature of from about 20° to 80° C., usually in a sealed reaction vessel in order to prevent the evaporation of the trialkylamine, for a period of between 16 and 96 hours to yield a hydrobromide salt.

In a second part, the hydrobromide salt prepared in the first part, is treated with a silver salt, e.g., silver carbonate, in the presence of a lower alkanol, e.g., methanol, at a temperature of from 0° to 40° C. for a period of between 15 minutes and 3 hours to yield a compound of formula VII.

More conveniently, it has been discovered that the compounds of subclass Ia where n is 2 may be prepared by a two-step reaction as set forth below employing a compound of formula IV as the starting material.

REACTION B1

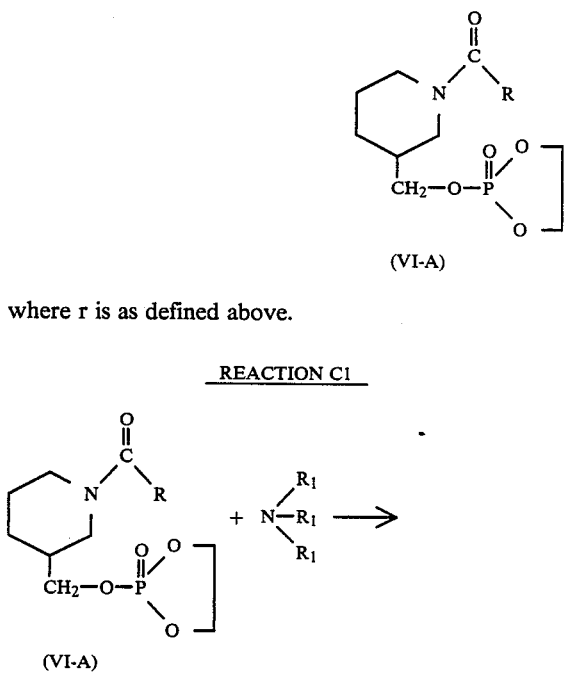

where r is as defined above.

REACTION C1

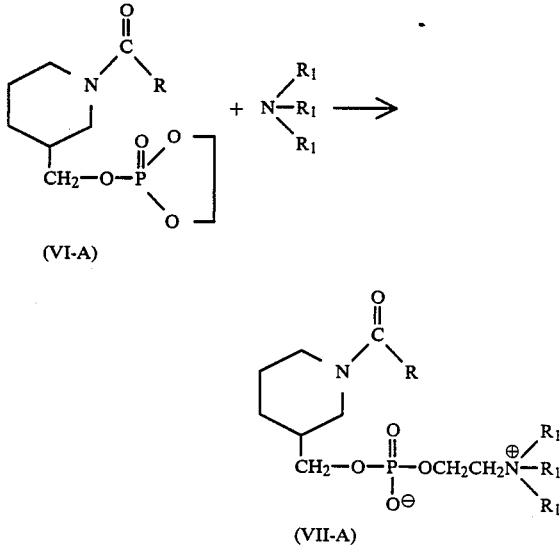

where R and each $R_1$ are as defined above.

In Reaction B1, a compound of formula IV, is reacted with 2-chloro-2-oxo-1,3,2-dioxaphospholane in the presence of an amine base such as pyridine or a trialkylamine, preferably triethylamine, to yield an intermediate adduct of formula VI-A. The reaction is conducted at a temperature of from about −20° to 30° C. for a period of between 1 and 24 hours.

Reaction C1 involves the reaction of an intermediate adduct of formula VI-A with a trialkylamine in the presence of an inert, organic solvent, e.g., an aromatic hydrocarbon such as benzene or toluene, an aliphatic halohydrocarbon such as chloroform or dichloromethane or a lower alkyl nitrile such as acetonitrile. The reaction is generally carried out at a temperture of from about 20° to 80° C., usually in a sealed reaction vessel to prevent the evaporation of the trialkylamine, for a period of between 16 and 96 hours to yield a compound of formula VII-A.

The compounds of subclass Ib may be prepared according to the following three-step reaction:

STEP A

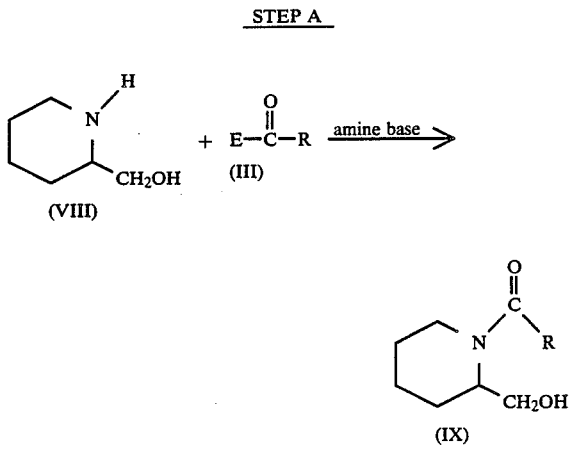

where E and R are as defined above.

STEP B

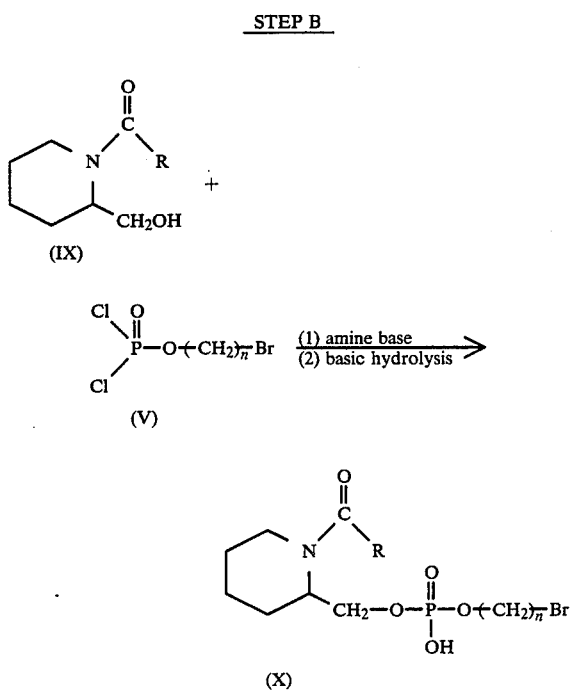

where R and n are as defined above.

STEP C

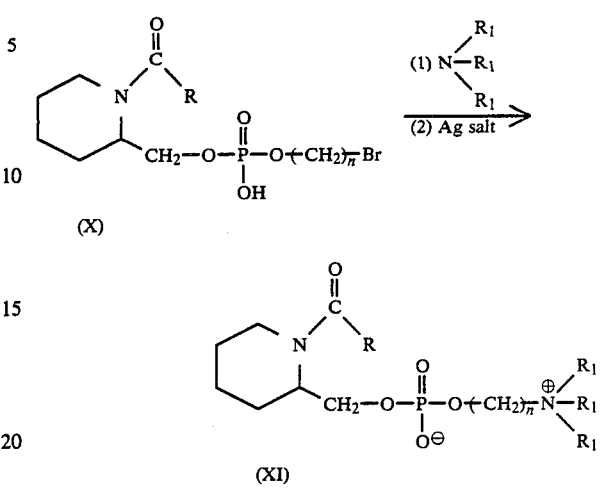

where R, each $R_1$ and n are as defined above.

As to the individual steps, Step A concerns the reaction of a compound of formula VIII with a carboxylic acid halide of formula III in the presence of an amine base such as pyridine or a trialkyl amine, preferably triethylamine, to yield a compound of formula IX. With regard to the reaction conditions, i.e., presence of solvents, reaction temperatures and reaction times, they are analogous to that set forth above in Reaction A.

Step B involves, in a first part, the reaction of compound prepared in Step A, i.e., a compound of formula IX, with a compound of formula V, i.e., a bromoalkoxydichlorophosphate compound, e.g., 2-bromoethoxydichlorophosphate, in the presence of an amine base, such as pyridine or triethylamine. The reaction conditions are essentially identical to those set forth above in the first part of Reaction B.

In the second part of Step B, the product produced in the first part is subjected to basic hydrolysis by suspending the product in water. The hydrolysis is conveniently carried out at a temperature of from 20° to 100° C. for a period of from 15 minutes to about 3 hours to yield a compound of formula X.

The last step, viz., Step C, is directed to the reaction of a compound prepared in Step B, i.e., a compound of formula X, with a trialkylamine in the presence of an inert, organic solvent, e.g., an aromatic hydrocarbon such as benzene or toluene, an aliphatic halohydrocarbon such as chloroform or dichloromethane or a lower alkyl nitrile such as acetonitrile to yield a hydrobromide salt. As to reaction temperatures and times, they are analogous to those set forth above in the first part of Reaction C.

As regards the second part of Step C, the hydrobromide salt prepared in the first part is treated with a silver salt, e.g., silver carbonate, in the presence of a lower alkanol, e.g., methanol, at a temperature of from 0° to 40° C. for a period of between 15 minutes and 3 hours to yield a compound of formula XI.

As with the compounds of subclass Ia, when it is desired to prepare a compound of subclass Ib where n is 2, it has been found more convenient to employ the following two step reaction utilizing a compound of formula IX as the starting material:

STEP B1

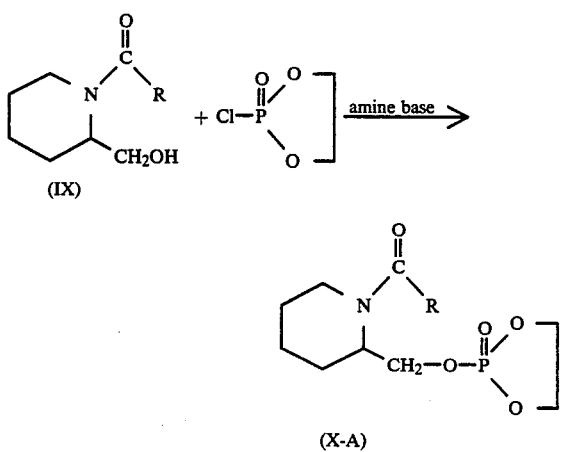

where R is as defined above.

STEP C1

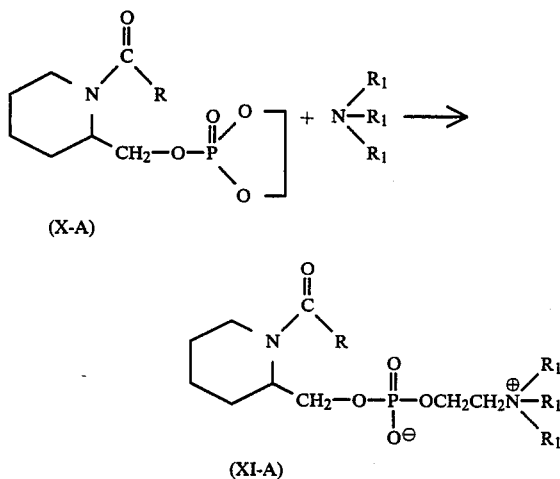

where R and each $R_1$ are as defined above.

The reaction of a compound of formula IX with 2-chloro-2-oxo-1,3,2-dioxaphospholane in the presence of an amine base as depicted in Step B1, and the reaction of a compound so produced, i.e., an intermediate adduct of formula X-A, with a trialkyl amine to yield a compound of formula XI-A, are conducted in an analogous manner to that set forth above in Reaction B1 and C1, respectively.

As to any of the particular starting materials set forth above, e.g., compounds of formulae II, III, V, etc., they are either known and obtained by methods described in the literature, or where not known, may be obtained by methods analogous to those described in the literature.

The product of each reaction may, if desired, be purified by conventional techniques such as recrystallization (if a solid), column chromatography, preparative thin layer chromatography, gas chromatography, (if sufficiently volatile) or fractional distillation under high vacuum (if sufficiently volatile). Often, however, the crude product of one reaction may be employed in the following reaction without purification.

As is evident to those skilled in the art, the compounds of formula I contain an asymmetric carbon atom. It should be understood, therefore, that the individual enantiomers are contemplated as being included within the scope of this invention.

As indicated above, all of the compounds of formula I are anti-tumor agents and are, therefore, useful in inhibiting the growth of various lymphomas, sarcomas, carcinomas, myelomas and leukemia cell lines. The anti-tumor activity of the compounds of formula I may be demonstrated employing the Tumor Cell Cytotoxicity test (TCC test) as follows:

In flat bottom microtiter plates (Nunc Roskilde, Denmark) were placed Abelson 8.1 lymphoma, YAC, L1210, P815, Meth A fibrosarcoma or fresh human neuroblastoma tumor cells in DMEM+10% fetal calf serum and the tumor cell-containing plates were incubated with 1,3 and 5 µg of the test compound for a period of 6 to 72 hours. The number of tumor cells present in the Abelson 8.1, YAC, L1210 and P815 assays was determined by measuring the alkaline phosphatase as follows:

The tumor cell plates were centrifuged (500×g) for ten minutes and the supernatant flicked off. Without further washing, 100 µl of buffer containing 20 µl of diethanolamine, 2 µM of $MgCl_2.6H_2O$, 2.5 µM of p-nitrophenylphosphate and 10 mg Triton X-100 were added. The samples were incubated for 60 minutes at room temperature and the enzymatic reaction was terminated by the addition of 100 µl of 0.5N NaOH. The absorbance was then measured at 405 nm using a Titertek Multiskan apparatus.

The number of tumor cells present in the Meth A fibrosarcoma and human neuroblastoma assays was measured by $^3H$-thymidine uptake as follows:

After 72 hours, the cells are thoroughly washed, and each well treated with ca. 0.1 µC $^3H$-thymidine. After 4-6 hours, the cells are collected using a commercial cell harvester, and the radioactivity in the filtrate is measured in a scintillation counter.

At a concentration of 5 µg and an incubation period of 72 hours, the following results were obtained:

|       | % Inhibition |     |      |      |        |       |
|-------|------|-----|------|------|--------|-------|
|       | Abel. | YAC | L1210 | P815 | Meth A | neuro. |
| Ex. 1 | 79   | 23  | 46   | 72   | 39     | 39    |

The anti-tumor activity of the compounds of formula I may also be demonstrated employing the Influence on Cytotoxicity of $ET-18-OCH_3$ test (IC-ET test) as follows:

Bone marrow cell macrophages ($10^5$/well) obtained from $[BALV/CX57/BL_6]F1$ mice were incubated with 10 µg of 1-octadecyl-2-methoxy-3-phosphoryl choline ($ET-18-OCH_3$) for 24 hours in flat bottom microtiter plates (Nunc Roskilde, Denmark), after which time they are centrifuged and washed once. Abelson 8.1 tumor cells in DMEM+10% fetal calf serum and 1,3 and 5 µg of the test compound were then added to the plates. With the cytotoxicity of $ET-18-OCH_3$ (10 µg) alone set at 100%, the inhibition or enhancement of the cytotoxic effect, as measured by an alkaline phosphatase assay, was determined and values recorded after 72 hours for 1,3 and 5 µg of the test substance. At a concentration of 3 µg of the compound of Example 1, a greater than 90% enhancement of the cytotoxic effect was observed.

The usefulness of the compounds of formula I in treating tumors may additionally be demonstrated employing the following procedure:

Meth A fibrosarcoma cells were induced in BALB/C mice by administering methylcholanthrene according to the procedure of Old, et al. (L. J. Old, E. A. Boyse, D. A. Clarke, and E. Carswell, Ann. N.Y. Acad. Sci., 101, 80 (1962). These tumor cells were harvested from the peritoneal cavity 10 to 12 days after administration of methylcholanthrene, Ten $CBF_1$ mice of 10-12 week age were each implanted with $7.3 \times 10^6$ Meth A sarcoma cells to serve as control. A second group of ten $CBF_1$ mice were each implanted with $7.3 \times 10^6$ Meth A sarcoma cells and on day one after implant Meth A sarcoma cells and on day one after implant each mouse was treated p.o. with 5-50 ug of the test compound per day for a total of twenty or twenty-seven days. Tumor growth and survivors were assayed on days 7, 14, 21 and 28 after tumor implantation. Under these conditions, none of the control group animals survived, whereas 9 out of the 10 animals which were administered 5 ug per day of the compound of Example 1 for 28 days not only survived but showed, as well, a reduction in the size of the tumor to 0.4% of the control.

The precise dosage of the compounds of formula I to be employed for inhibiting tumors depends upon several factors including the host, the nature and the severity of the condition being treated, the mode of administration and the particular compound employed. However, in general, satisfactory inhibition of tumors is achieved when a compound of formula I is administered orally or intravenously at a daily dosage of 1-100, preferably 5-35 mg/kg body weight or, for most larger primates, a daily dosage of 500-2000 mg, preferably 1000-1500 mg. A typical oral dosage is 400 mg, two to three times a day, or 20 mg/kg intravenously over a 24 hour period.

Usually, a small dosage is administered initially and the dosage is gradually increased until the optimal dosage for the host under treatment is determined. For parenteral administration, e.g., i.v. or i.p., a dosage somewhat lower than would be used for oral administration of the same compound to the same host having the same condition is usually employed. The upper limit of dosage is that imposed by side effects, and can be determined by trial for the host being treated, including humans.

A typical dosage unit for oral administration may contain 300 to 600 mg of a compound of formula I. Preferred oral dosage units contain 300 to 500 mg, especially 350 to 450 mg of a compound of formula I.

The compounds of formula I may be combined with one or more pharmaceutically acceptable carriers and, optionally, one or more other conventional pharmaceutical adjuvants and administered orally in the form of tablets, dispersible powders, granules, capsules, elixirs, suspensions and the like or parenterally in the form of sterile injectable solutions or suspensions. The compositions may be prepared by conventional means.

The compounds of formula I may be formulated into such pharmaceutical compositions containing an amount of the active substance that is effective for inhibiting tumors, such compositions in unit dosage form and such compositions comprising a solid pharmaceutically acceptable carrier.

Tablets and capsules containing the ingredients indicated below may be prepared by conventional techniques and are useful as anti-tumor agents. The tablet may be administered two to four times a day whereas the capsule is suitably administered three times a day.

| Ingredients | Weight (mg) tablet | capsule |
|---|---|---|
| compound of formula I, e.g. the compound of Example 1 | 400 | 400 |
| tragacanth | 10 | — |
| lactose (spray-dried) | 197.5 | 250 |
| corn starch | 25 | — |
| talcum | 15 | — |
| magnesium stearate | 2.5 | — |
| Total | 650.0 | 650 |

The preferred pharmaceutical compositions from the standpoint of preparation and ease of administration are solid compositions, particularly liquid or hard-filled capsules and tablets containing from about 350 to 450 milligrams of the active ingredient.

The following examples show representative compounds encompassed by this invention and their synthesis. However, it should be clearly understood that they are for purposes of illustration only.

EXAMPLE 1

2-Hydroxy-[1-octadecyloxycarbonyl-3-piperidinyl methoxy]phosphinyloxy]-N,N,N-trimethylethaneaminium hydroxide inner salt-4-oxide

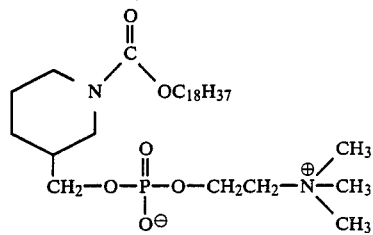

(a) Preparation of 3-hydroxymethyl-N-octadecyloxycarbonyl piperidine

To a solution of 10.52 g (91 mmol) of 3-piperidinemethanol in 100 ml of dichloromethane, and 13.3 ml (96 mmol) of triethylamine was added, at room temperature, a solution of 87 mmol of octadecylchloroformate in toluene. The resultant mixture was then allowed to react for 24 hours, after which time it was washed with water. The aqueous layer was then extracted twice with dichloromethane and the organic layers were combined, dried with magnesium sulfate and filtered. The solvent was then removed in vacuo to yield the crude product as a solid. The crude product was then chromatographed on silica gel employing dichloromethane as the eluent to yield a white solid.

Preparation of the title compound 0.5 g (1.22 mmol) of the compound prepared in (a) above was dissolved in 20 ml of benzene containing 15 mg of N,N-dimethylaminopyridine and 0.21 ml (1.52 mmol) of triethylamine. To the mixture was added 0.23 g (1.62 mmol) of 2-chloro-2-oxo-1,3,2-dioxaphospholane and the resultant mixture was stirred at room temperature for 2 hours. The salts were then removed by filtration and the residue taken up in dry acetonitrile which was then cooled to −78° C. Trimethylamine was then condensed therein, the reaction vessel was capped, warmed to 60° C. and maintained at this temperature for 24 hours. The reaction mixture was then cooled in an ice-methanol bath and the solids were then isolated by filtration, washed with acetonitrile and dried under vacuum to yield the crude product. The crude product was then chromatographed on silica gel employing a mixture of chloroform, methanol and water (in a 2:1:0.2 ratio) as the eluent to yield a white solid, m.p., >230° C.

EXAMPLE 2

2Hydroxy-[1-hexadecyloxycarbonyl-3-piperidinylmethoxy]phosphinyloxy]-N,N,N-trimethylethaneaminium hydroxide inner salt-4-oxide

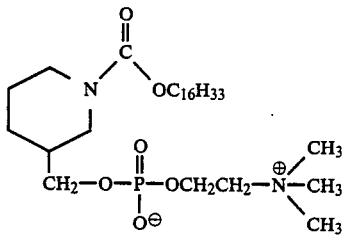

(a) Preparation of N-hexadecyloxycarbonyl-3-hydroxymethyl piperidine

Following essentially the procedure of Example 1(a), and using in place of octadecyl chloroformate, an approximately equivalent amount of hexadecyl chloroformate, a white solid was obtained.

Preparation of the title compound

Following essentially the last step of the procedure in preparing the compound of Example 1, and using in place of the compound prepared in 1(a), an approximately equivalent amount of the compound prepared in (a) above, a white solid was obtained, m.p. >230° C.

EXAMPLE 3

2-Hydroxy-[1-hexadecanoyl-3-piperidinyl methoxy]phosphinyloxy]-N,N,N-trimethylethaneaminium hydroxide inner salt-4-oxide

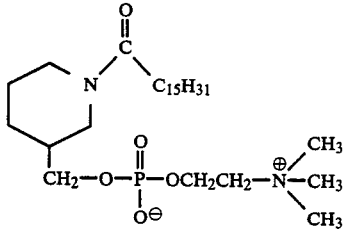

(a) Preparation of N-hexadecanoyl-3-hydroxymethyl piperidine

Following essentially the procedure of Example 1(a), and using in place of octadecyl chloroformate, an approximately equivalent amount of palmitoyl chloride, a white solid was obtained.

(b) Preparation of the title compound

Following essentially the last step of the procedure in preparing the compound of Example 1, and using in place of the compound prepared in 1(a), an approximately equivalent amount of the compound prepared in (a) above, a white solid was obtained, m.p. 229° C.

EXAMPLE 4

2-Hydroxy-[1-hexadecyloxycarbonyl-2-piperidinyl methoxy]phosphinyloxy]-N,N,N-trimethylethaneaminium hydroxide inner salt-4-oxide

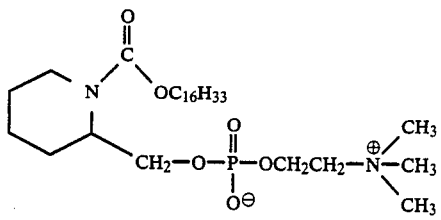

(a) Preparation of N-hexadecyloxycarbonyl-2-hydroxymethyl piperidine

Following essentially the procedure of Example 1(a), and using in place of 3-piperidinemethanol, an approximately equivalent amount of 2-piperidinemethanol, and using in place of octadecyl chloroformate, an approximately equivalent amount of hexadecyl chloroformate, a white solid was obtained.

Preparation of the title compound

Following essentially the last step of the procedure in preparing the compound of Example 1, and using in place of the compound prepared in 1(a), an approximately equivalent amount of the compound prepared in (a) above, a white solid was obtained, m.p. >230° C.

EXAMPLE 5

6-Hydroxy-[1-octadecyloxycarbonyl-3-piperidinyl methoxy]phosphinyloxy]-N,N,N-trimethylhexaneaminium hydroxide inner salt-8-oxide

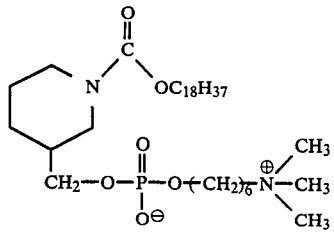

To 10 ml of dry benzene containing 0.358 g (1.2 mmol) of 6-bromohexyloxyphosphorodichloridate was added 0.411 g (1.0 mmol) of the compound of Example 1(a) and the resultant mixture was cooled in an ice-salt bath, after which time it was treated dropwise, under a nitrogen atmosphere, with a solution of 103 μl of pyridine in 1 ml of benzene.

The ice-salt bath was then removed and the mixture allowed to warm to room temperature over a period of 6 hours. The volatiles were then removed under reduced pressure and the residue was suspended in 15 ml of water and heated in the steam bath for 1 hour. The mixture was then cooled to room temperature, extracted with chloroform and the extracts dried over magnesium sulfate, filtered and the solvent removed in vacuo. The residue was then treated with trimethylamine in a manner analogous to that described above in the last step in the preparation of Example 1 to afford the hydrobromide salt of the title compound. The hydrobromide salt was then taken up in 10 ml of methanol into which 0.310 g of silver carbonate was suspended. After 90 minutes, the solids were removed by filtration and the filtrate concentrated in vacuo to yield the crude product. The crude product was then chromatographed on silica gel employing a mixture of chloroform, methanol and water (in a 2:1:0.2 ratio) as the eluent to yield a white solid, m.p. 137°–140° C.

What is claimed is:

1. A compound of formula Ia''':

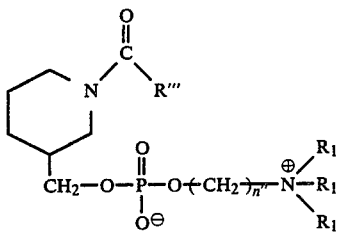 Ia''' where
R'' is n-$C_{12}$-$C_{18}$ alkoxy;
n'' is an integer 2 to 4; and
each $R_1$, independently, is $C_1$-$C_3$ alkyl.

2. A method of treating tumors selected from the group consisting of Abelson 8.1 lymphoma, YAC, L1210, P815, Meth A fibrosarcoma and human neuroblastoma comprising administering to a subject afflicted therewith a therapeutically effective amount of a compound according to claim 1.

3. A method according to claim 2 comprising administering to a mammal in need of such treatment a therapeutically effective amount of the compound of the formula:

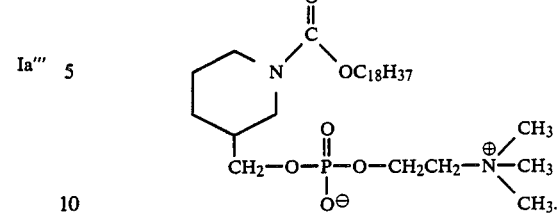

4. A pharmaceutical composition useful in treating tumors comprising a pharmaceutically acceptable carrier and a therapeutically effective amount of a compound according to claim 1.

5. A compound according to claim 1 having the formula

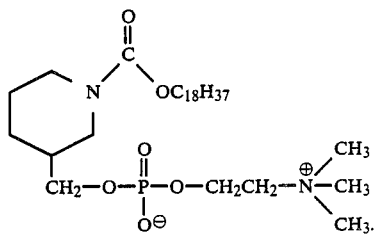

* * * * *